United States Patent
Griffin, III

(10) Patent No.: US 10,754,325 B1
(45) Date of Patent: Aug. 25, 2020

(54) CERAMIC PROCESSING FOR THE DIRECT MANUFACTURE OF CUSTOMIZED LABIAL AND LINGUAL ORTHODONTIC BRACKETS

(71) Applicant: LightForce Orthodontics, Inc, Cambridge, MA (US)

(72) Inventor: Alfred Charles Griffin, III, Boston, MA (US)

(73) Assignee: LightForce Orthodontics, Inc, Cambridge, MA (US)

( * ) Notice: Subject to any disclaimer, the term of this patent is extended or adjusted under 35 U.S.C. 154(b) by 0 days.

(21) Appl. No.: 16/357,052

(22) Filed: Mar. 18, 2019

Related U.S. Application Data

(63) Continuation of application No. 15/041,895, filed on Feb. 11, 2016, now Pat. No. 10,241,499.

(60) Provisional application No. 62/114,898, filed on Feb. 11, 2015.

(51) Int. Cl.

| | |
|---|---|
| G05B 19/4099 | (2006.01) |
| A61B 6/14 | (2006.01) |
| A61C 9/00 | (2006.01) |
| A61B 6/00 | (2006.01) |
| A61B 6/03 | (2006.01) |
| A61C 7/14 | (2006.01) |

(Continued)

(52) U.S. Cl.
CPC .......... *G05B 19/4099* (2013.01); *A61B 6/032* (2013.01); *A61B 6/14* (2013.01); *A61B 6/4085* (2013.01); *A61C 7/141* (2013.01); *A61C 7/145* (2013.01); *A61C 7/146* (2013.01); *A61C 7/16* (2013.01); *A61C 7/20* (2013.01); *A61C 9/006* (2013.01); *G05B 2219/35134* (2013.01)

(58) Field of Classification Search
None
See application file for complete search history.

(56) References Cited

U.S. PATENT DOCUMENTS

| 4,639,218 A | 1/1987 | Jones et al. |
|---|---|---|
| 2003/0165790 A1 | 9/2003 | Castro et al. |
| 2007/0207435 A1 | 9/2007 | Devanathan |

(Continued)

OTHER PUBLICATIONS

Silver M, Griffin AC, Jr., Azzopardi L, Masoud MI, Tokede O, Griffin AC, 3rd. Novel methods reveal that parallelism contributes to the functional vertical slot dimension in ceramic and metal brackets. The Angle orthodontist. Nov. 2018;88(6):812-818.

(Continued)

*Primary Examiner* — Cory W Eskridge
(74) *Attorney, Agent, or Firm* — Smith, Gambrell & Russell, LLP

(57) ABSTRACT

A method of manufacturing customized ceramic labial/lingual orthodontic brackets by digital light processing, said method comprises measuring dentition data of a profile of teeth of a patient, wherein measuring dentition data is performed using a CT scanner or intra-oral scanner, based on the dentition data, creating a three dimensional computer-assisted design (3D CAD) model of the patient's teeth using reverse engineering, and saving the 3D CAD model on a computer, designing a 3D CAD bracket structure model for a single labial or lingual bracket structure, importing the 3D CAD bracket structure model into a Digital Light Processing (DLP) machine, directly producing the bracket by layer manufacturing.

18 Claims, 7 Drawing Sheets

(51) Int. Cl.
*A61C 7/16* (2006.01)
*A61C 7/20* (2006.01)

(56) References Cited

U.S. PATENT DOCUMENTS

| | | | |
|---|---|---|---|
| 2008/0015727 A1* | 1/2008 | Dunne | A61B 5/4547 |
| | | | 700/118 |
| 2011/0309554 A1 | 12/2011 | Liska et al. | |
| 2014/0170591 A1 | 6/2014 | El-Siblani | |
| 2016/0256240 A1 | 9/2016 | Shivapuja et al. | |

OTHER PUBLICATIONS

Krey KF, Darkazanly N, Kuhnert R, Ruge S. 3D-printed orthodontic brackets—proof of concept. Int J Comput Dent. 2016;19(4):351-362.
Interview with Johannes Homa, CEO of Lithoz GmbH, Advanced Manufacturing Insight, Aug. 11, 2014.
Wohlers Report 2001, Part 6, p. 144.
William R. Proffit DDS PhD, Contemporary Orthodontics. 5th ed. St. Louis, MO. Mosby Elsevier; 2013, pp. 369, 374.
John C. Bennett, Fundamentals of Bracket Selection, 2nd ed. London, UK. 2010, pp. 14, 42.

* cited by examiner

CERAMIC PROCESSING FOR THE DIRECT MANUFACTURE OF CUSTOMIZED LABIAL AND LINGUAL ORTHODONTIC BRACKETS

CROSS-REFERENCE TO RELATED PATENT APPLICATION(S)

This patent application is a continuation of U.S. non-provisional patent application Ser. No. 15/041,895, filed Feb. 11, 2016, now U.S. Pat. No. 10,241,499, issued Mar. 26, 2019, which claims the benefit of U.S. provisional application 62/114,898, filed Feb. 11, 2015, the contents of which are all incorporated in their entirety herein.

BACKGROUND OF THE INVENTION

1. Field of the Invention

An embodiment of present invention relates generally to the manufacturing of ceramic labial/lingual orthodontic brackets for straightening the teeth and correcting malocclusion. More specifically, an embodiment of the invention relates to the methodology of direct manufacture of customized labial/lingual orthodontic brackets by using lithography-based ceramic manufacturing (LCM) or by digital light processing of ceramics (DLP) additive manufacturing (AM) technology.

2. Description of the Related Art

Orthodontics has been widely adapted in clinics to correct malocclusion and straighten teeth. The traditional method is to adhere preformed brackets onto the teeth and run elastic metal wires of round, square, or rectangular cross-sectional shape through the bracket slots to provide the driving force. The adaptation of the bracket to the individual tooth is performed by filling the gap between the tooth surface and bracket surface with adhesive. This thereby bonds the bracket to the tooth such that the bracket slot, when the teeth are moved to their final position, lies in a near flat (depending on manufacturing accuracy) horizontal plane.

Preformed edgewise brackets may have no prescription, requiring adjustment of the archwire. Alternatively, the edgewise brackets may have an idealized prescription of angulation, inclination, or in/out variation for specific teeth in what is referred to as a "straight-wire appliance". Because the bracket pad is typically not custom made for an individual patient's tooth, the clinician is responsible for the bracket placement, which may introduce a source of error, which commonly increases patient visits and overall treatment time. These brackets are typically off-the-shelf products, and currently there are no custom designed ceramic brackets available commercially. A misplacement in bonding a bracket to a tooth can be corrected by compensation bends in the wire or by debonding and repositioning of the bracket, both of which increase time and cost. Custom metal lingual brackets are currently available that are fabricated at a central location from 3D scans or impressions of the dentition and mailed back to the clinician and transferred to the patient via indirect bonding. Selective laser melting (SLM) is a 3DAM technique that has been used to create custom metal lingual brackets (for example, see U.S. Pat. No. 8,694,142 B2), but this technique suffers from insufficient resolution and surface finish. While true custom labial brackets have been used, custom positioning of a standard, non-custom bracket can be created via indirect bonding which itself has inherent error within the bracket itself.

Many current true custom labial systems (SURESMILE™ Inc.) rely heavily on putting custom bends in the wire based on a 3D scan rather than creating a true straight-wire appliance. For example, U.S. Pat. No. 8,690,568 provides for a method to weld a metal bracket slot to a stock metal bracket base into a custom position, but does not describe a method for creating a custom bracket base or to create an aesthetic, non-metal bracket. These partially custom metal brackets suffer from inaccuracy in slot position and premature debonding due a stock bracket base that doesn't match the tooth morphology, and are unappealing to older patients who prefer to have non-metal brackets for aesthetic concerns.

Ceramic brackets have been commercially available and studied since the 1980s and are a desirable material compared to metal brackets due to their excellent esthetics, resistance to creep, rigidity, biocompatibility, corrosion resistance, stability in the oral environment and non-toxic nature. Currently, no system for creating an esthetic custom lingual or labial ceramic orthodontic brackets exists, and no custom bracket system exists that may be fabricated 100% in-office by trained members of a private orthodontic practice.

A need arises for more efficient and accurate techniques for creating custom lingual and labial ceramic orthodontic brackets, and more aesthetic labial brackets

SUMMARY OF THE INVENTION

An embodiment of the present invention provides improved techniques for creating custom lingual or labial ceramic orthodontic brackets, and which provides the capability for in office fabrication of such brackets.

An embodiment of the present invention may be used to solve problems occurring in the current manufacturing techniques of straight wire appliance orthodontic brackets. For example, in one embodiment, it may provide a direct manufacturing method of customized lingual/labial brackets by utilizing digital light processing (DLP). Examples of items that may be produced include customized brackets according to individual features, and which include more adhesive brackets on the tooth surface because of the high manufacturing accuracy. DLP additive manufacturing AM may be performed in a device small enough to comfortably fit in a private orthodontic lab and can currently be obtained at a reasonable price, given the market price and in-office volume for non-custom and custom brackets.

For example, in one embodiment, a method of manufacturing customized ceramic labial/lingual orthodontic brackets by digital light processing may comprise measuring dentition data of a profile of teeth of a patient, based on the dentition data, creating a three dimensional computer-assisted design (3D CAD) model of the patient's teeth using reverse engineering, and saving the 3D CAD model on a computer, designing a 3D CAD bracket structure model for a single labial or lingual bracket structure, importing data related to the 3D CAD bracket structure model into a Digital Light Processing (DLP) machine, directly producing the bracket in the DLP machine by layer manufacturing.

The 3D CAD bracket structure model may include data representing at least a) the bracket pad (bottom plate) that has recesses and/or undercuts into the bonding surface of the bracket, to contact a particular tooth's surfaces, b) slots for positioning according to the orthodontia needs of the patient, c) a bracket material, d) the particular tooth's profile, and e) a bracket guide to guide 3-dimensional placement of the bracket onto the tooth.

The DLP machine may comprise a molding compartment comprising a platform and a plunger to directly produce the bracket by layer manufacturing, a material compartment, and an LED light source for digital light processing, wherein the bracket is produced by layer manufacturing using slicing software to separate the 3D CAD bracket structure model into layers and to get a horizontal section model for each layer so that a shape of each layer produced by the DLP machine is consistent with the 3D CAD structure data. The DLP machine may comprise a vat adapted to hold the bracket during manufacturing, a horizontal build platform adapted to be held at a settable height above the vat bottom, an exposure unit, adapted to be controlled for position selective exposure of a surface on the horizontal build platform with an intensity pattern with predetermined geometry, a control unit, adapted to receive the 3D CAD bracket structure model and, using the 3D CAD bracket structure model to polymerize in successive exposure steps layers lying one above the other on the build platform, respectively with predetermined geometry, by controlling the exposure unit, and to adjust, after each exposure step for a layer, a relative position of the build platform to the vat bottom, to build up the object successively in the desired form, which results from the sequence of the layer geometries. The exposure unit may further comprise a laser as a light source, a light beam of which successively scans the exposure area by way of a movable mirror controlled by the control unit.

Directly producing the bracket by layer manufacturing may further comprise in an apparatus comprising a vat with an at least partially transparently or translucently formed horizontal bottom, into which light polymerizable material can be filled, a horizontal build platform adapted to be held at a settable height above the vat bottom, an exposure unit adapted to be controlled for position selective exposure of a surface on the build platform with an intensity pattern with predetermined geometry, comprising a light source refined by micromirrors to more precisely control curing, a control unit adapted for polymerizing in successive exposure steps layers lying one above the other on the build platform, controlling the exposure unit so as to selectively expose a photo-reactive slurry in the vat, adjusting, after each exposure for a layer, a relative position of the build platform to the vat bottom, and building up the bracket successively in the desired form, resulting from the sequence of the layer geometries. The exposure unit may further comprise a laser as a light source, a light beam of which successively scans the exposure area by way of a movable mirror controlled by the control unit.

A scanning accuracy may be less than 0.02 mm. A manufacturing accuracy may be from 5 to about 60 μm, and wherein the accuracy may be achieved by using a between layer additive error compensation method that predicts an amount of polymerization shrinkage. Manufactured layers of the bracket comprise a material selected from the group consisting of high strength oxide ceramics including Aluminum Oxide ($Al_2O_3$) and Zirconium Oxide ($ZrO_2$) and may be mono- or polycrystalline ceramic. The smallest length from a bracket pad to slot depth may be from 0.2 mm-3 mm depending on the bracket offset required and desire to reduce the bracket profile for patient comfort.

The 3D CAD model may be saved as an .stl file. The thickness of the manufactured layers may be from 5 to 100 micrometers (μm). Different light curing strategies (LCSs) and depths of cure (Cd) may be used. A selection of material for producing layers of the bracket may be based on different force demands. The printed bracket guides may have a single bracket attachment for a single bracket. An adhesive material may be used to hold the bracket on the ceramic archwire. The adhesive material may be sticky wax. Indirect bonding/custom bracket placement may occur via a tray (for example, a silicone based or vacuum formed tray) that carries the said custom ceramic brackets to the ideal tooth location.

The printed brackets may have a metal insert that contacts the archwire in the slot. The printed brackets may be of a traditional twin design or are modified to be self-ligating or active ligating and are designed to accommodate 0.018 in or 0.022 in archwires in the slot, but slot height may vary from 0.018-0.022. The bracket angulation, offsets, torque, and prescription may be determined based on a chosen treatment. The structural properties of the base may be altered to facilitate easier debonding of the bracket following treatment. A part of the bracket may be a pre-formed green ceramic body that functions to decrease the time and complexity of the printed bracket. The method may further comprise producing a bracket guide comprising a rigid ceramic rectangular archwire or other archform that dictates a position of each bracket on a tooth in every plane with at least two occlusal/incisal supports adapted to help place brackets via an indirect bonding system. A part of the bracket that holds or connects the bracket to the tooth surface may be designed based on a surface profile of the tooth. The bracket may have a color that is matched to a color of a tooth to which the bracket is to be attached. The bracket may be clear. The bracket may have a selected color unrelated to a color of a tooth to which the bracket is to be attached.

The DLP machine may include a light source that is a laser or LED light source. A light source of the DLP machine may radiate a wavelength between 400 and 500 nm. The DLP machine may include a digital light processing chip as light modulator. The digital light processing chip may be a micromirror array or an LCD array.

Measuring dentition data may be performed using a CT scanner, intra-oral scanner, a coordinate measuring machine, a laser scanner, or a structured light digitizers. Measuring dentition data may be performed by conducting 3D scanning on a casted or 3D printed teeth model.

The light-polymerizable material may be selected from the group consisting of high strength Oxide ceramics including Aluminum Oxide ($Al_2O_3$) and Zirconium Oxide ($ZrO_2$). A slot position relative to the tooth may be customized by manufacturing a custom base or by manufacturing a custom slot position where a base is unchanged.

DETAILED DESCRIPTION OF THE INVENTION

An embodiment of the present invention provides improved techniques for creating custom lingual or labial ceramic orthodontic brackets, and which provides the capability for in-office fabrication of such brackets.

Figure 1:
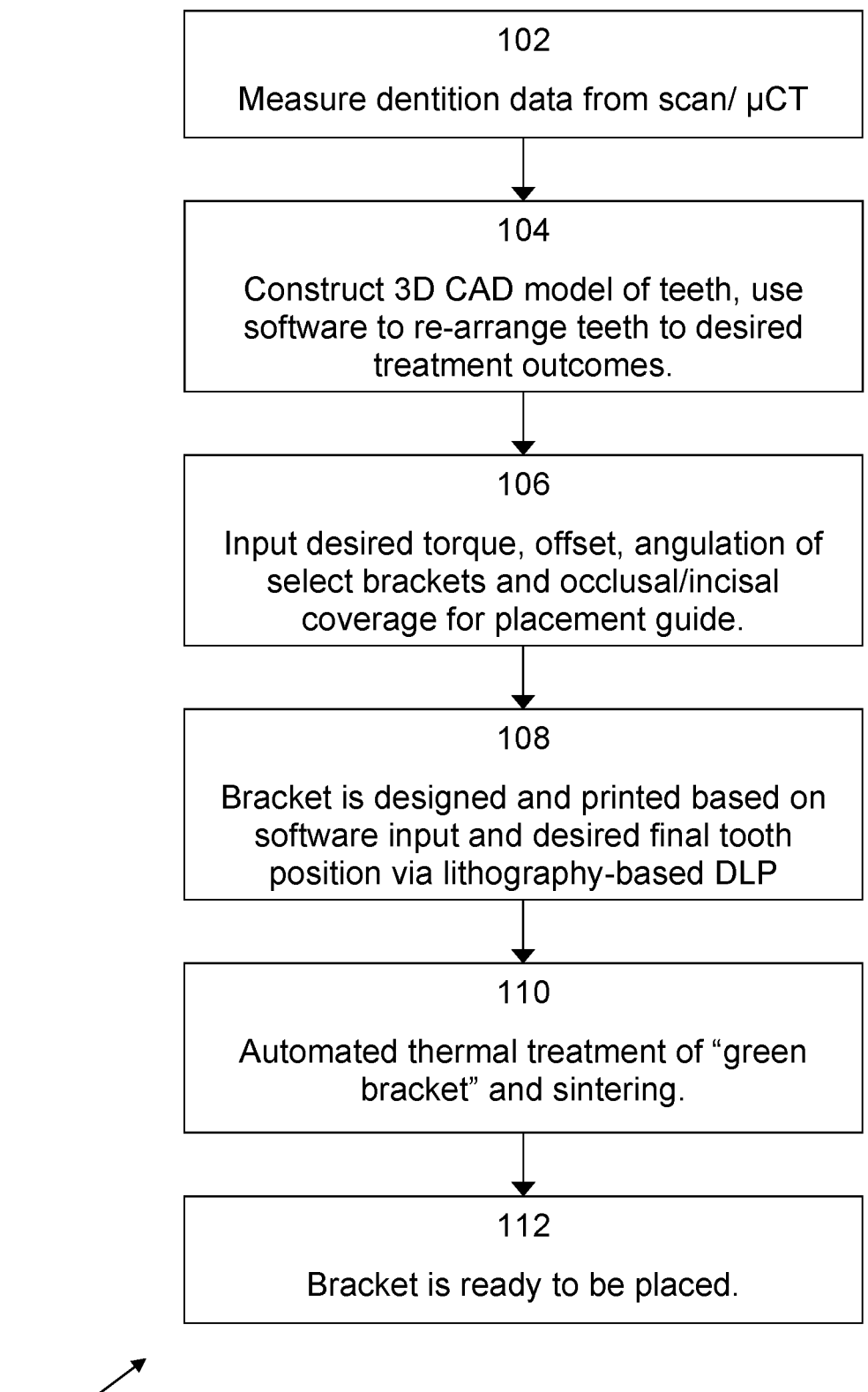
FIG. 1 is an exemplary flow diagram of an embodiment of a process for direct manufacturing lingual or labial orthodontic brackets.

An exemplary flowchart of an embodiment a direct manufacturing process 100 of lingual or labial orthodontic brackets by digital light processing is shown in FIG. 1. The process begins with 102, in which dentition data is measured and the parameters of the tooth profile are analyzed. For example, such measurement may use CT layer scanning a non-contact 3D scanner or an intra-oral scanner directly on the patient's teeth, or may use 3D readings on a teeth model previously cast or 3D printed using a coordinate measuring machine, a laser scanner, or a structured light digitizer. The scanning accuracy of such techniques is typically less than 0.02 mm.

In 104, based on the given dentition data, a 3D CAD model of the measured teeth is constructed based on the dentition data and saved in the computer in a typical file format, such as the .stl file format. The exterior structure of teeth is complicated, usually including irregular curves. The software may then be used to re-arrange the teeth in the model to the desired treatment outcomes that may be based on the long-axis of a tooth.

In 106, additional information, such as the desired torque, offset, angulation of select brackets and occlusal/incisal coverage for placement guide is entered.

In 108, the bracket (or brackets) is designed by the software based on the input 3D CAD model of the measured teeth, the model of the desired treatment outcomes, and the input additional information. The output of the design process may be a 3D CAD model. Such a 3D CAD model may be designed for a single lingual/labial bracket structure, including the bracket guide and bracket pad in contact with teeth surface, as well as the slots for the ideal position according to the orthodontia requirement, ceramic bracket material, and tooth profile. A bracket guide may be a single bracket pad for a single bracket or may be a rigid ceramic rectangular archwire with two or more occlusal supports, which are designed to help place brackets via indirect bonding. If the guide is for a single bracket, the bracket guide may be printed such that it is serrated at its interface with the bracket such that it may be snapped or drilled off upon bonding.

Figure 2:
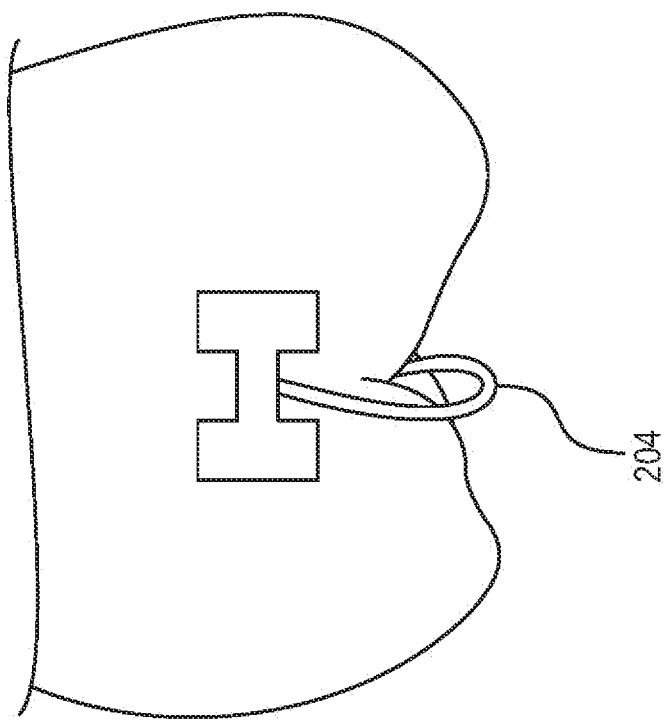
FIG. 2 illustrates an example of a single bracket bracket-guide showing a lower molar and upper incisor tooth.
Figure 2:
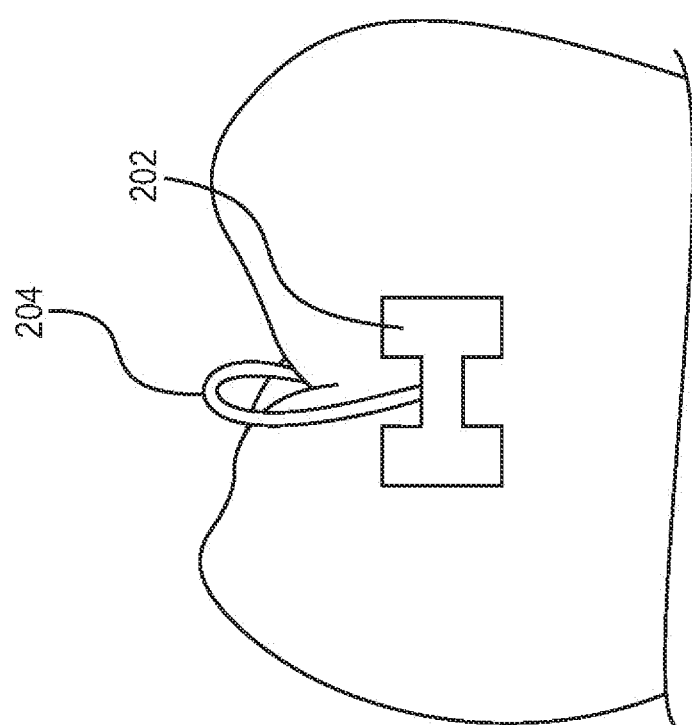
Figure 3:
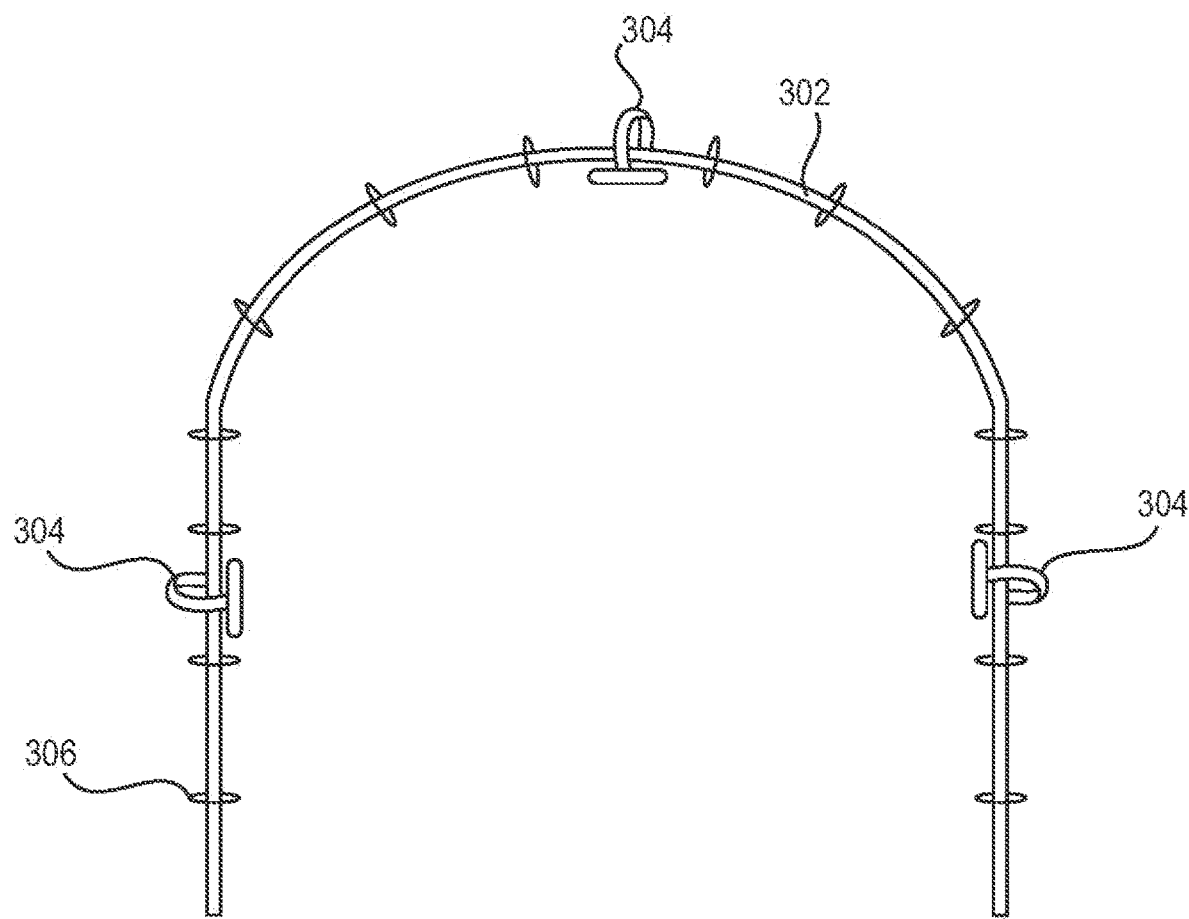
FIG. 3 illustrates an example of a bracket guide that may be a rigid ceramic rectangular archwire that engages each bracket in every plane with two or more occlusal supports.

3D CAD bracket structure models of labial or lingual brackets may be designed by computer according to the orthodontic requirements, material, and teeth morphology. Referring to FIG. 2, which illustrates an example of a single bracket bracket-guide showing a lower molar and upper incisor tooth with a connected, but detachable bracket guide that may have a weak point or serration at the guide-bracket interface. The bracket model design may include the bracket pad 202 (bonding pad) contacting with the tooth surface, as well as the custom bracket slot located on its ideal position and a bracket guide 204. A bracket guide 204 may be a single bracket pad 202 attached to a single bracket guide 204, as shown in FIG. 2. Alternatively, as shown in FIG. 3, a bracket guide may be a rigid ceramic rectangular archwire that engages each bracket in every plane with two or more occlusal supports 304 that are designed to help place brackets via indirect bonding. The horizontal ceramic wire and the occlusal/incisal pads control for vertical position. Vertical notches such as 306 on the wire control the horizontal position of the bracket on the ceramic wire.

3D CAD bracket structure models are processed to generate manufacturing control data for use by the production equipment. For example, where DLP equipment is used to produce the brackets, the software slices the 3D CAD bracket structure models to separate it into thin layers and get the horizontal section model for each layer. Based on this section model, the DLP equipment can directly produce ceramic brackets, ensuring the shape of each layer is consistent to the 3D CAD structure data. For example, the thickness of such layers may be about 20 μm to about 50 μm (micrometers or microns) with a manufacturing accuracy of about 5 μm to about 10 μm by using between-layer additive error compensation.

Returning to 108 of FIG. 1, the 3D CAD bracket structure model is transmitted to or imported into a 3D production machine, such as a DLP machine and the ceramic brackets are produced. In the case of DLP, the brackets may be produced by digital light processing directly.

Digital light processing (DLP) is another 3D additive manufacturing (AM)process that works by stacking layers of a photocurable resin with an Aluminum Oxide ($Al_2O_3$) or Zirconium Oxide ($ZrO_2$) solid loading, and followed by a thermal debinding and sintering step. The higher resolution of this process is made possible by the LED light's digital mirror device (DMD) chip and optics used. Lithography-based ceramic manufacturing (LCM) has improved this process making it more accurate with higher resolution (40 μm) and rigidity. The new LCM process involves the selective curing of a photosensitive resin containing homogenously dispersed oxide or glass ceramic particles that can be fabricated at very high resolution due to imaging systems which enable the transfer of layer information by means of ever-improving LED technology.

In 110, post-processing may then be applied. For example, a thermal treatment (for binder burnout) and a sintering process may be applied to achieve optimal or improved ceramic density. For example, the debinding and sintering phase may include removing the green bracket from the device, exposing the blank to a furnace to decompose the polymerized binder (debinding), and sintering of the ceramic material.

The pad (bonding pad) of the bracket may be less than 0.4 mm thick. The bracket placement guide may be placed occlusally/incisally to guide the correct placement of the bracket on the tooth. Examples of raw materials of the brackets may include powder of high strength oxide ceramics such as Aluminum Oxide ($Al_2O_3$) and Zirconium Oxide ($ZrO_2$), or other high strength ceramic compositions.

The base of bracket may be adhered to the tooth surface and the bracket slot may be matched to the archwire. According to requirements of mechanical properties, different composition of material may be required for the layers during the DLP manufacturing process. After being built up, the brackets may have a gradient and better performance.

Further, the bracket surface may be processed based on clinical demand.

Returning to FIG. 1, in 112, the bracket is ready to be placed.

Typically, the thickness of the bracket pad may less than 1 mm for lingual brackets and less than 1.5 for labial brackets. Suitable manufacturing materials may include high-strength Oxide ceramics, such as Aluminum Oxide ($Al_2O_3$) and Zirconium Oxide ($ZrO_2$). The bracket pad may be adhered to the tooth surface with well-known dental adhesives. The bracket slot may be matched to the archwire, which may be straight or custom bent. Depending upon the manufacturing process used, different ceramics or composition of powder may be required for the layers. For example, if a selective laser melting manufacturing process is used, an LED light source may be used for the selective curing of a photosensitive resin containing the oxide or glass ceramic particles. Different layers may use different ceramics or compositions of powder.

Figure 4:
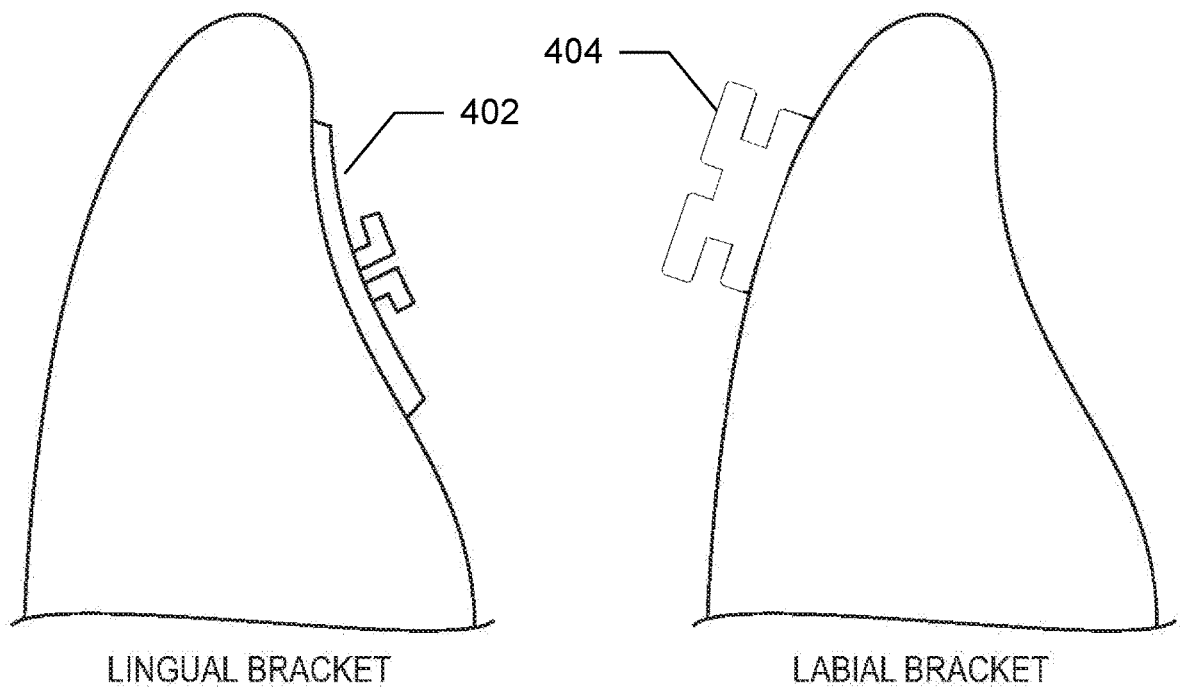
FIG. 4 illustrates an example of designed brackets having a custom bracket pad that is matched to the lingual or labial surface of the tooth.

The bracket pad, which holds or connects the bracket to the tooth surface, may be designed specifically according to the tooth surface profile, instead of a generalized gridding pattern. The customized brackets can meet individual case demand, such as increased anterior labial crown torque required in certain types of cases. For example, as shown in FIG. 4, the curve on tooth surface and the designed bracket, the tooth side of the bracket (bracket pad) is matched to the lingual or labial surface of the tooth, for example for lingual bracket 402 and labial bracket 404.

Figure 5:
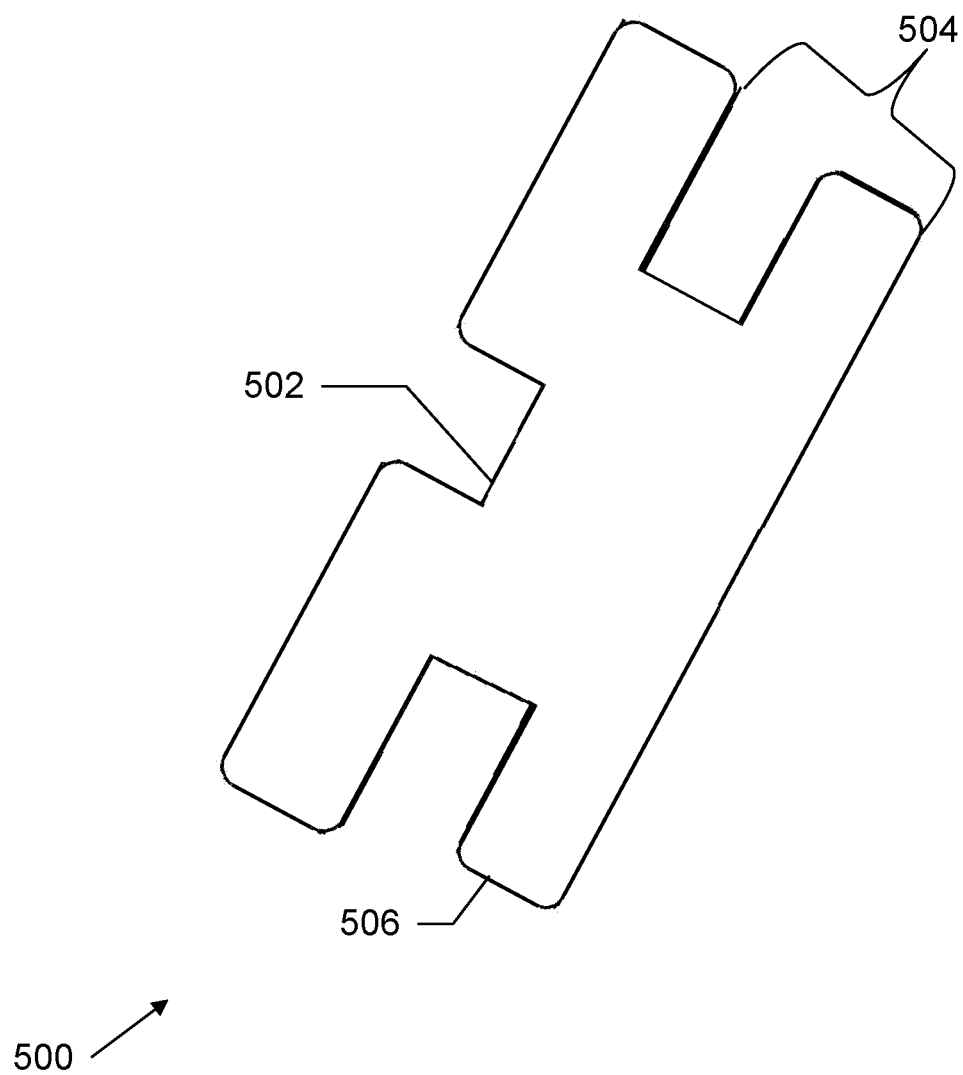
FIG. 5 illustrates a side view of an example of a designed bracket.

A side view of an exemplary printed bracket 500 is shown in FIG. 5. The slot 502 on the bracket may have high accuracy in size, shape, and angler, and may have low thickness and is designed to accommodate a rectangular wire when completely filled. Slot 502 may be manufactured to any desired size and shape, but typically, slot 502 is manufactured with a greater depth than height or width. The base 504 of the bracket may have different height because of the selected material or desired orthodontic result. Likewise, the pad 506 of the bracket may highly match the tooth surface and maximize the tooth contact surface. This may allow for more accurate bracket placement by the clinician and better bond approximation to the tooth. Also, because each slot has its own position and shape to cooperate with the archwire, twisting error may be minimized and improved orthodontic result may be actualized. In a number of embodiments, these features may be manufactured as one piece and that the customization of the slot relative to the tooth may be a function of the slot changing position or the bracket base moving. In many embodiments, no machining of the features is required to produce a suitable bracket.

Figure 6:
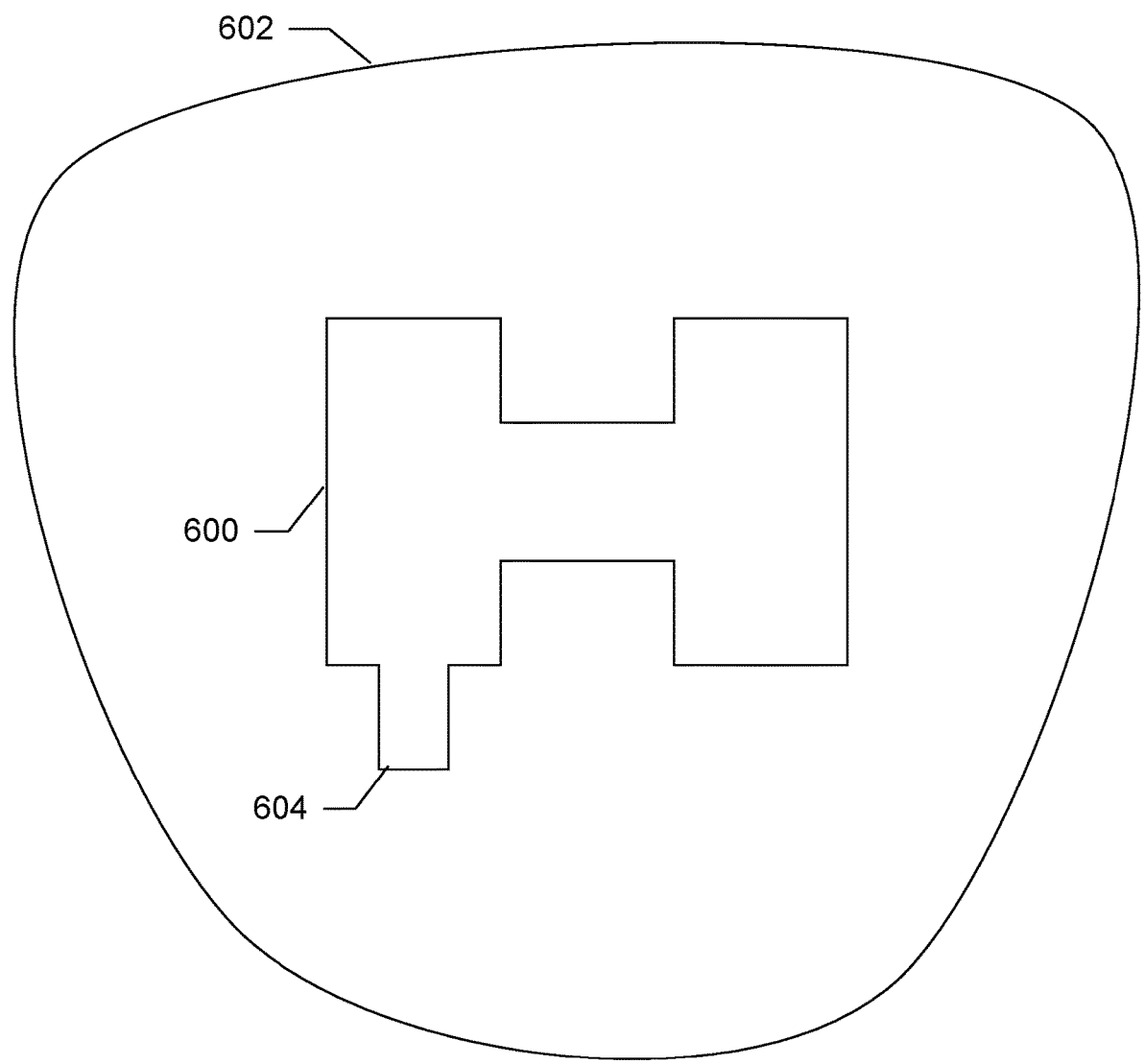
FIG. 6 illustrates a top view of an example of a designed bracket.

A top view of an exemplary printed bracket 600 is shown in FIG. 6. Bracket guides may be printed that extend an arm occlusally/incisally that attaches to a pad that covers enough of the structure of the tooth 602 (mesial/distal of occlusal/incisal surface or marginal ridge) such that brackets are placed in the computer-generated ideal location to create the desired tooth position. A bracket guide may be a single bracket pad for a single bracket or may be a rigid ceramic rectangular archwire that engages each bracket in every plane with two or more occlusal supports that are designed to help place brackets via indirect bonding. The horizontal ceramic wire and the occlusal/incisal pads control for vertical position, vertical notches on the wire control the horizontal position of the bracket on the ceramic wire guide.

Bracket 600 may further include an attachment such as a hook 604 that provides the capability to use additional delivery systems such as elastomers, springs or other attachments that create vectors of force. In a number of embodiments, these features may be manufactured as one piece, protruding from any predesigned area to create the proper force vectors desired, and no machining of the features is required to produce a suitable bracket.

Using the lithography-based digital light processing technique can turn the designed model into a ceramic product rapidly. The bracket manufacturing involves few steps and can be done on site, saving time and cost.

The described techniques may be used to manufacture brackets from various Oxide ceramics and light-curable materials such as Aluminum Oxide ($Al_2O_3$) and Zirconium Oxide ($ZrO_2$).

The described techniques may be used to attain a true straight wire appliance where bracket placement accuracy is improved, thus reducing treatment time and error; or may also be used in conjunction with a custom-bent arch wire to achieve ideal results.

Patients currently pay higher fees for white-colored ceramic brackets over metal due to their increased esthetics. For example, many patients desire a bracket that matches the color of the tooth to which the bracket is attached. This may cause the bracket to be less visible and provide improved appearance. As another example, embodiments of the present invention may provide the capability to produce clear brackets, which may provide still improved appearance. Additionally, embodiments of the present invention may provide the capability to produce brackets in almost any color desired or selected, for example, in bright colors for use in children and some adults. Likewise, embodiments of the present invention may provide the capability to produce brackets having visible shapes that are not dictated by function, such as in the shape of animals, vehicles, toys, etc., for example, for use in children and some adults.

The described techniques may be made cost-effective to the point where an individual orthodontic practice could purchase the required equipment and software. This would provide the capability to simplify their bracket inventory instead of stocking brackets of different prescriptions.

Digital light processing (lithography-based) of ceramics has many advantages for orthodontic bracket fabrication over selective laser sintering/melting (SLM) which uses thermal energy, and 3-D printing (3DP) systems that use a binder and polymer-derived ceramics (PDCs). For example, DLP may provide higher surface quality, better object resolution, and improved mechanical properties. PDCs structured using light in a stereolithographic or mask exposure process may also be used as a ceramic AM method for bracket fabrication.

Custom lingual brackets may be fabricated by this method, which may receive a pre-bent customized archwire as described by US 2007/0015104 A1. Custom labial brackets may also receive pre-bent wires.

The procedure for the layering additive manufacturing (AM) methodology of the labial/lingual orthodontic brackets by lithography-based DLP (U.S. Pat. No. 8,623,264 B2) is as follows.

An example of a lithography-based DLP process is described in U.S. Pat. No. 8,623,264 B2, which is incorporated herein by reference, but may be briefly summarized as follows: a light-polymerizable material, the material being located in at least one trough, having a particularly light-transmissive, horizontal bottom, is polymerized by illumination on at least one horizontal platform, the platform having a pre-specified geometry and projecting into a trough, in an illumination field, wherein the platform is displaced vertically to form a subsequent layer, light-polymerizable material is then added to the most recently formed layer, and repetition of the foregoing steps leads to the layered construction of the orthodontic bracket in the desired prescription/mold, which arises from the succession of layer geometries determined from the CAD software. The trough can be shifted horizontally to a supply position, and the supply device brings light-polymerizable material at least to an illumination field of the trough bottom, before the at least one trough is shifted to an illumination position in which the illumination field is located below the platform and above the illumination unit, and illumination is carried out, creating a "green bracket".

The light-polymerizable material or photo-reactive suspension (slurry) can be prepared based on commercially available di- and mono-functional methacrylates. An example material might be a slurry blend of 0.01-0.025 wt % of a highly reactive photoinitiator, 0.05-6 wt % a dispersant, an absorber, and 2-20 wt % of a non-reactive diluent. A solid loading of high strength Oxide ceramics such as Aluminum Oxide ($Al_2O_3$) and Zirconium Oxide ($ZrO_2$) powder can be used, but this process may extend to other ceramic materials.

Figure 7:
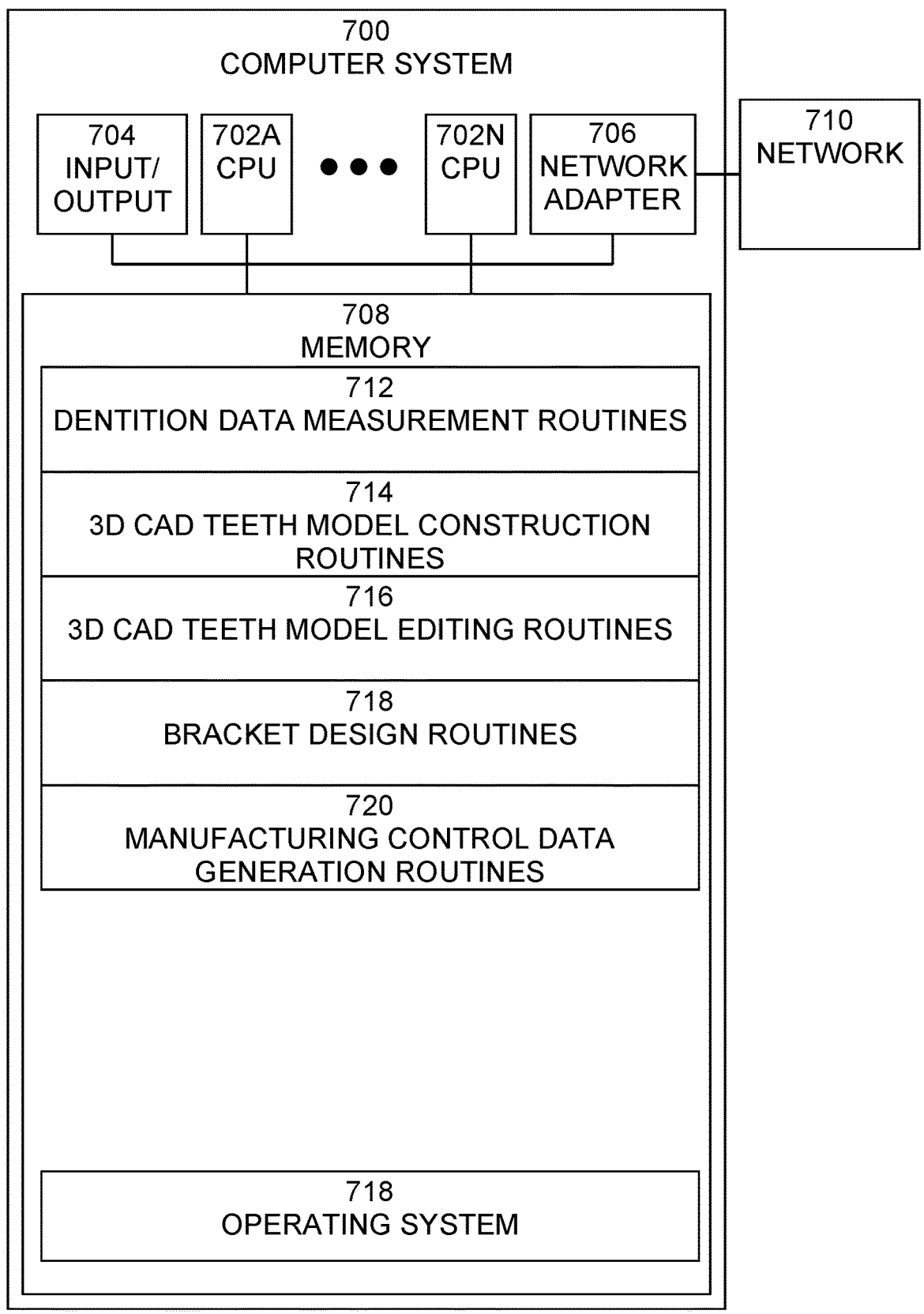
FIG. 7 is an exemplary block diagram of an embodiment of a computer system in which the processes of the present invention may be implemented.

An exemplary block diagram of a computer system 700, in which the processes shown above may be implemented, is shown in FIG. 7. Computer system 700 is typically a programmed general-purpose computer system, such as a personal computer, workstation, server system, and minicomputer or mainframe computer. Computer system 700 includes one or more processors (CPUs) 702A-702N, input/output circuitry 704, network adapter 706, and memory 708. CPUs 702A-702N execute program instructions in order to carry out the functions of embodiments of the present invention. Typically, CPUs 702A-702N are one or more microprocessors, such as an INTEL PENTIUM® processor. FIG. 7 illustrates an embodiment in which computer system 700 is implemented as a single multi-processor computer system, in which multiple processors 702A-702N share system resources, such as memory 708, input/output circuitry 704, and network adapter 706. However, the present invention also contemplates embodiments in which computer system 700 is implemented as a plurality of networked computer systems, which may be single-processor computer systems, multi-processor computer systems, or a mix thereof.

Input/output circuitry 704 provides the capability to input data to, or output data from, computer system 700. For example, input/output circuitry may include input devices, such as keyboards, mice, touchpads, trackballs, scanners, etc., output devices, such as video adapters, monitors, printers, etc., and input/output devices, such as, modems, etc. Network adapter 706 interfaces device 700 with a network 710. Network 710 may be any public or proprietary LAN or WAN, including, but not limited to the Internet.

Memory 708 stores program instructions that are executed by, and data that are used and processed by, CPU 702 to perform the functions of computer system 700. Memory 708 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 708 varies depending upon the function that computer system 700 is programmed to perform. In the example shown in FIG. 7, memory contents that may be included in a system in which a content analysis platform is implemented are shown. However, one of skill in the art would recognize that these functions, along with the memory contents related to those functions, may be included on one system, or may be distributed among a plurality of systems, based on well-known engineering considerations. Embodiments of the present invention contemplate any and all such arrangements.

In the example shown in FIG. 7, memory 708 may include dentition data measurement routines 712, 3D CAD teeth model construction routines 714, 3D CAD teeth model editing routines 716, bracket design routines 718, manufacturing control data generation routines 720, and operating system 722. Dentition data measurement routines 712 may obtain and process dentition data, such as may be generated by CT layer scanning or a non-contact 3D scanner directly on the patient's teeth, or uses 3D readings on the teeth model previously cast. 3D CAD teeth model construction routines 714 may construct a 3D CAD model of the measured teeth based on the dentition data. 3D CAD teeth model editing routines 716 may be used to re-arrange the teeth in the model to the desired treatment outcomes and may additionally be used to accept additional information, such as the desired torque, offset, angulation of select brackets and occlusal/incisal coverage for placement guide. Bracket design routines 718 may be used to design and generate a 3D CAD model based on the input 3D CAD model of the measured teeth, the model of the desired treatment outcomes, and the input additional information. Manufacturing control data generation routines 720 may be used to generate manufacturing control data for use by the production equipment. Operating system 722 provides overall system functionality.

It is to be noted that additional functionality may be implemented in end user devices, such as end user devices 104 shown in FIG. 1. End user systems may be computer systems having a structure similar to that shown in FIG. 7. Such end user systems may include geometric analysis routines to perform geometric analysis of a location of an advertisement or content, such as may be performed by step 302 of FIG. 3. Likewise, such end user systems may include resource-based analysis routines to determine whether a computer is optimizing an advertisement or content for display on the screen, such as may be performed by step 302 of FIG. 3.

As shown in FIG. 7, an embodiment of the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

It is important to note that while aspects of the present invention may be implemented in the context of a fully functioning data processing system, those of ordinary skill in the art will appreciate that the processes of an embodiment of the present invention are capable of being distributed in the form of a computer program product including a computer readable medium of instructions. Examples of non-transitory computer readable media include storage media, examples of which include, but are not limited to, floppy disks, hard disk drives, CD-ROMs, DVD-ROMs, RAM, and, flash memory.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method of manufacturing customized ceramic labial/lingual orthodontic brackets by digital light processing, said method comprising:
   measuring dentition data of a profile of teeth of a patient, wherein a scanning accuracy of the measuring is less than 0.02 mm;
   based on the dentition data, creating a three dimensional computer-assisted design (3D CAD) model of the patient's teeth using reverse engineering;
   re-arranging the patient's teeth in the model to a desired treatment outcome based on a long-axis of at least one tooth;
   designing a 3D CAD bracket structure model for a single labial or lingual orthodontic bracket structure including a slot;
   slicing the 3D CAD bracket structure model to separate it into thin layers to obtain a horizontal section model for each layer;
   importing data related to the 3D CAD bracket structure model into a photo-reactive slurry-based Digital Light Processing (DLP) machine;
   directly producing the ceramic bracket in the DLP machine by layer manufacturing, wherein a manufacturing accuracy is from 5 to about 60 μm, and wherein a thickness of the manufactured layers is from 5 to 100 micrometers (μm) based on resolution requirements of the bracket area.

2. The method of claim 1, wherein the single labial or lingual orthodontic bracket structure including a slot comprises a bracket guide and bracket pad in contact with a tooth surface.

3. The method of claim 2, wherein the bracket guide is a single bracket pad for a single bracket.

4. The method of claim 3, wherein the bracket guide is printed such that it is serrated at its interface with the bracket so as to be snapped or drilled off upon bonding.

5. The method of claim 2, wherein the bracket guide is a rigid ceramic rectangular archwire with a plurality of occlusal supports.

6. The method of claim 5, wherein the rigid ceramic rectangular archwire comprises a plurality of vertical notches to control a horizontal position of the bracket on the rigid ceramic rectangular archwire.

7. The method of claim 5, wherein the rigid ceramic rectangular archwire is custom-bent.

8. The method of claim 1, wherein the bracket has a visible shape that is not dictated by function.

9. The method of claim 1, wherein the bracket has visible shape comprising one of:
   a shape of at least one animal;
   a shape of at least one vehicle; or
   a shape of at least one toy.

10. A customized ceramic labial/lingual orthodontic bracket produced by digital light processing, the bracket comprising:
    a plurality of layers of ceramic directly produced in a digital light processing machine by layer manufacturing, the shape of each layer consistent with 3D CAD structure data obtained by:
      measuring dentition data of a profile of teeth of a patient, wherein a scanning accuracy of the measuring is less than 0.02 mm,
      based on the dentition data, creating a three dimensional computer-assisted design (3D CAD) model of the patient's teeth using reverse engineering,
      re-arranging the patient's teeth in the model to a desired treatment outcome based on a long-axis of at least one tooth,
      designing a 3D CAD bracket structure model for a single labial or lingual orthodontic bracket structure including a slot, and
      slicing the 3D CAD bracket structure model to separate it into thin layers to obtain a horizontal section model for each layer;
    wherein a manufacturing accuracy of the bracket is from 5 to about 60 μm, and wherein a thickness of the manufactured layers is from 5 to 100 micrometers (μm) based on resolution requirements of the bracket area.

11. The method of claim 10, wherein the single labial or lingual orthodontic bracket structure including a slot comprises a bracket guide and bracket pad in contact with a tooth surface.

12. The method of claim 11, wherein the bracket guide is a single bracket pad for a single bracket.

13. The method of claim 12, wherein the bracket guide is printed such that it is serrated at its interface with the bracket so as to be snapped or drilled off upon bonding.

14. The method of claim 13, wherein the bracket guide is a rigid ceramic rectangular archwire with a plurality of occlusal supports.

15. The method of claim 14, wherein the rigid ceramic rectangular archwire comprises a plurality of vertical notches to control a horizontal position of the bracket on the rigid ceramic rectangular archwire.

16. The method of claim 15, wherein the rigid ceramic rectangular archwire is custom-bent.

17. The method of claim 10, wherein the bracket has a visible shape that is not dictated by function.

18. The method of claim 10, wherein the bracket has visible shape comprising one of:
    a shape of at least one animal;
    a shape of at least one vehicle; or
    a shape of at least one toy.

* * * * *